United States Patent [19]
Salyer

[11] Patent Number: 5,236,433
[45] Date of Patent: Aug. 17, 1993

[54] TOOL DRIVER

[75] Inventor: Brian D. Salyer, Warsaw, Ind.

[73] Assignee: Othy, Inc., Warsaw, Ind.

[21] Appl. No.: 696,949

[22] Filed: May 8, 1991

[51] Int. Cl.$^5$ .............................................. A61B 17/16
[52] U.S. Cl. ........................................ 606/91; 606/80; 606/81; 606/86
[58] Field of Search ..................................... 606/79–81, 606/91; 269/47, 52; 279/22, 30, 57, 75

[56] References Cited

U.S. PATENT DOCUMENTS

| | | | |
|---|---|---|---|
| 1,130,716 | 3/1915 | Dressel | 279/75 X |
| 3,947,047 | 3/1976 | Hultman | 279/22 X |
| 3,975,032 | 8/1976 | Bent et al. | 279/30 |
| 4,692,073 | 9/1987 | Martindell | 279/75 X |
| 4,716,894 | 1/1988 | Lazzeri et al. | 606/91 |
| 4,811,632 | 3/1989 | Salyer | 76/24.1 X |
| 4,878,918 | 11/1989 | Tari et al. | 606/91 X |
| 4,900,202 | 2/1990 | Wienhold | 279/75 X |
| 5,013,194 | 5/1991 | Wienhold | 279/75 X |
| 5,037,424 | 8/1991 | Aboczsky | 606/91 |
| 5,061,270 | 10/1991 | Aboczsky | 606/91 |

FOREIGN PATENT DOCUMENTS 2236019 2/1973 Fed. Rep. of Germany ........ 279/75

Primary Examiner—Robert A. Hafer
Assistant Examiner—G. Stone
Attorney, Agent, or Firm—Lundy & Associates

[57] ABSTRACT

A tool driver which has a body having a bore. The bore has a longitudinal axis. A plunger is disposed in the bore. The body and the plunger have a lock. An actuator is disposed on the body. The actuator and the plunger are loosely coupled. The actuator is axially movable relative to the body and the plunger between a locked position and a retracted position. The actuator, in the locked position, substantially immobilizes the plunger relative to the body. The actuator and the plunger are axially movable together, relative to the body, between the retracted position and an extended position.

20 Claims, 4 Drawing Sheets

TOOL DRIVER

BACKGROUND OF THE INVENTION

The present invention pertains to holders for rotary tools and more particularly pertains to a tool driver suitable for use with acetabular reamer cups or other similarly shaped tools.

Acetabular reamer cups are surgical tools, which are used to cut hemispherical cavities in pelvis bones for the insertion of artificial hip joints. Acetabular reamer cups are mounted on tool drivers, which in turn are mounted in the chuck or collet of a portable drill or flexible powered shaft. Acetabular reamer cups are separable from their tool drivers to replace or sharpen as used. It may be necessary to change cups during an operation, for example. Tool drivers are not inexpensive and must be cleaned and reused.

Some previous tool drivers usable with acetabular reamer cups grip the cup by means of a flange and slot and an opposed spring-loaded ball catch, like that on a socket wrench or socket driver. This presents a problem in that the catch tends to trap dried blood, which is very difficult to remove during cleaning. An additional problem is that unless tolerances of cups and tool drivers are made very close, at greatly increased cost, there is considerable free play between the cup and tool driver. This increases wear and decreases the precision of the tool.

An alternative tool driver usable with acetabular reamer cups, described in Salyer, U.S. Pat. No. 4,811,632, issued on Mar. 14, 1989, has a cam and follower mechanism, which provides for axial and rotary movement of a clamp. That driver avoids many of the problems presented by the ball catch, but requires a separate locking mechanism and two handed use.

It is therefore highly desirable to provide an improved tool driver.

It is also highly desirable to provide an improved tool driver which can tightly grip and easily release an acetabular reamer cup.

It is also highly desirable to provide an improved tool driver which can be completely disassembled for cleaning.

It is also highly desirable to provide an improved tool driver which does not tend to catch bone debris.

It is also highly desirable to provide an improved tool driver which can be joined to or disjoined from an acetabular reamer cup with one hand.

It is finally highly desirable to provide an improved tool driver which meets all of the above desired features.

SUMMARY OF THE INVENTION

It is an object of the invention to provide an improved tool driver.

It is another object of the invention to provide an improved tool driver which can tightly grip and easily release an acetabular reamer cup.

It is another object of the invention to provide an improved tool driver which can be completely disassembled for cleaning.

It is another object of the invention to provide an improved tool driver which does not tend to catch bone debris.

It is another object of the invention to provide an improved tool driver, which can be joined to or disjoined from an acetabular reamer cup with one hand.

It is finally an object of the invention to provide an improved tool driver which meets all of the above desired features.

In the broader aspects of the invention there is provided a tool driver which has a body having a bore. The bore has a longitudinal axis. A plunger is disposed in the bore. The body and the plunger each have a clamp surface. The clamp surfaces are opposed. An actuator is disposed on the body. The actuator and the plunger are loosely coupled. The actuator is axially movable relative to the body and the plunger between a locked position and a retracted position. The actuator, in the locked position, substantially immobilizes the plunger relative to the body. The actuator and the plunger are axially movable together, relative to the body, between the retracted position and an extended position. The movement of the plunger between the extended position and the retracted position varies the separation of the clamp surfaces.

BRIEF DESCRIPTION OF THE DRAWINGS

The above mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
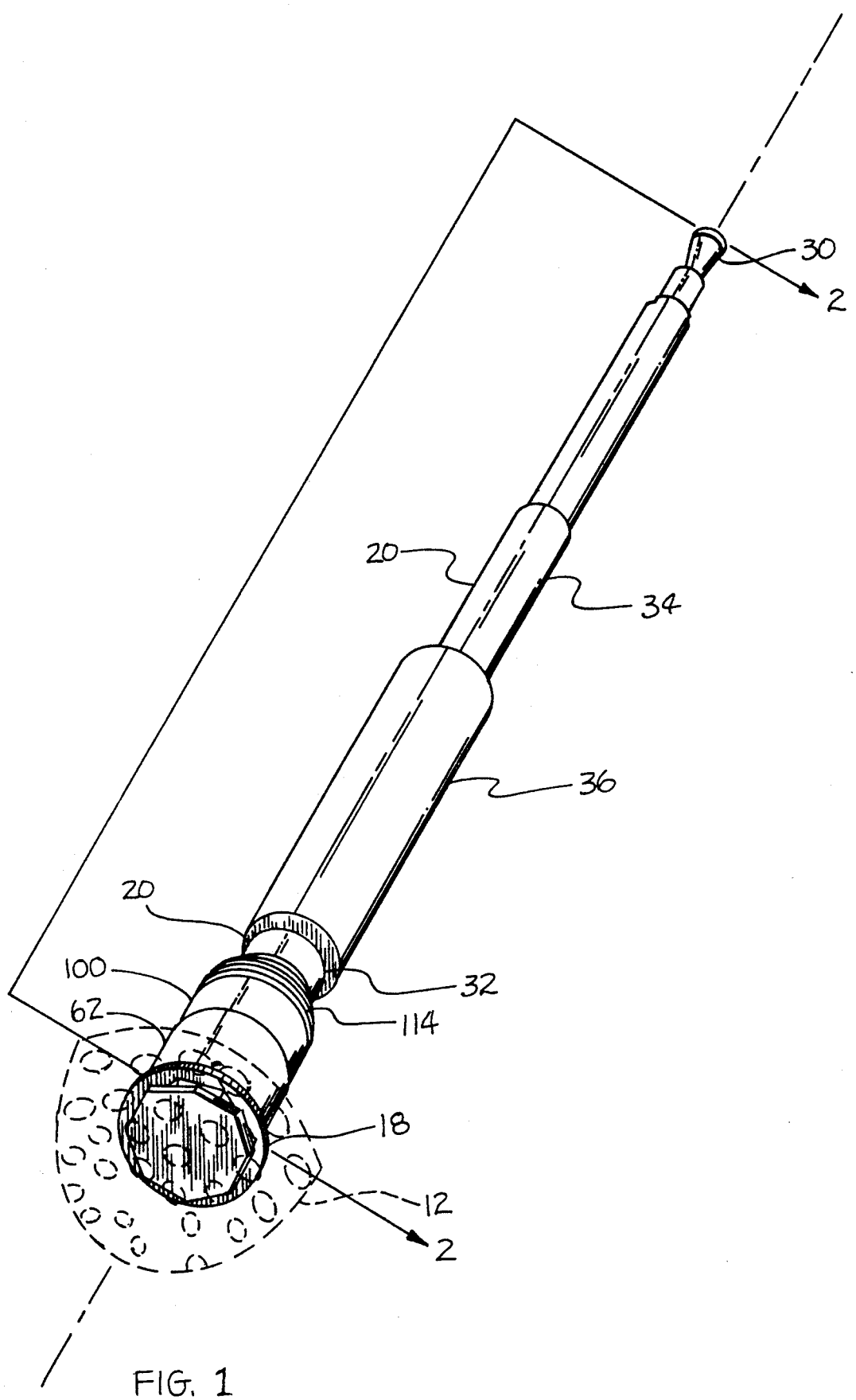
FIG. 1 is a perspective view of an embodiment of the tool driver of the invention. An acetabular reamer cup, held by the tool driver, is indicated by dashed lines. Engaged threads of front and rear parts of the tool driver body are indicated by dashed lines.

The tool driver 10 of the invention grips the base 12 of an acetabular reamer cup at the front end 13 and is clasped by a chuck or other holder of a portable drill or rotary shaft (not shown) at the other or rear end 30. Tool driver 10 has a longitudinal axis 14 and an elongate body 16. Body 16 has a flange 18 at end 13, and a shaft 20 extending between flange 18 and rear end 30.

Flange 18 is roughly annular in shape and has a centrally positioned boss 22 and a forwardly facing clamp surface 24 to the outside of boss 22. Boss 22 has a base surface 26, which is forward of clamp surface 24 and a boss shoulder 28, which is annular in shape and extends in a direction substantially parallel to longitudinal axis 14, between base surface 26 and clamp surface 24. Boss shoulder 28 defines a shape, in cross-sections radial to longitudinal axis 14, which is complementary to that of the opening in the base 12 of an acetabular reamer cup with which the tool driver is desirably used.

Shaft 20 extends rearwardly from flange 18 to a rear end 30. The configuration of rear end 30 is determined by the drill chuck, collet, or holder and may be varied, as necessary. Shaft 20 has a generally circular cross-section. In the particular embodiment shown in the figures, body 16 has separable front and rear parts 32, 34 joined together by engaged threads, which have the same direction of rotation for tightening as the direction of rotation of tool driver 10 during use. A sleeve 36 fits on a reduced diameter segment 38 of forward part 32. Sleeve 36 is sized to fit loosely and freely rotate, but be held in place axially by the adjoining segment 40 of front part 32 and by rear part 34. Sleeve 36 is desirably made of a material such as nylon, which provides low frictional resistance without lubrication.

A bore 42 extends coaxially into body 16 from the center of base surface 26. Within shaft 20, bore 42 defines a shaft wall 44. Bore 42 has a pair of main bore sections 46 and an enlarged bore section 48 therebetween. Main bore sections 46 are cylindrical in shape and have the same diameter. Enlarged bore section 48 is between main bore sections 46 and is generally cylindrical with a larger diameter than main bore sections 46.

A shaft slot 50 extends through shaft 20 in the form of a pair of opposed shaft subslots 52 extending through shaft wall 44 on both sides of bore 42. Subslots 52 are oval in shape and are aligned with each other axially. The longest dimension of subslots 52 is parallel to longitudinal axis 14. Subslots 52 each extend from the "rear" end of enlarged bore section 48 forward beyond the "front" end of enlarged bore section 48. "Front" and "rear" are used to connote their adjacency to front 13 and rear 30 ends. Shaft slot 50 has forward and rear secondary engagement edges 54, 56, respectively, at forward and rear ends of shaft slot 50.

A pair of opposed ball receivers 58 extend through shaft wall 44, to the rear of shaft slot 50. Ball receivers 58 are aligned with each other axially. Each ball receiver 58 communicates with bore 42 at an axial separation rearwardly from enlarged bore section 48. The shape of ball receivers 58 is generally cylindrical, however, adjoining bore 42, each ball receiver 58 has a ball restriction (not shown) which has a reduced diameter. Interposed in each ball receiver 58 is a lock ball or lock rotary element 60. The diameter of lock balls 60 is slightly less than that of ball receivers 58, but slightly greater than that of the ball restriction, and thus, lock balls 60 cannot pass through its restriction. The diameter of lock balls 60 is greater than length of each ball receiver 58 in a direction radial to axis 14.

A collar 62 is joined to and extends rearwardly from flange 18, in spaced relation to shaft 20. Collar 62 is cylindrical in shape and coaxial with body 16. In a particular embodiment of the invention, collar 62 and body 16 are monolithic, that is, made of a single piece of material. This eliminates any seam between body 16 and collar 62 allowing dirt therebetween or which could collect dirt, and eliminates any possibility of collar 62 and body 16 disassembling during use. A compression coil spring 64 encircles shaft 20 and contacts flange 18. Spring 64 is resiliently compressible from an axial length about equal to or longer than that of collar 62 to an axial length about one-half the axial length of collar 62. Spring 64 extends between flange 24 and actuator 100 as mentioned hereinafter. Spring 64 is positioned between body 16 and collar 62.

A plunger 66 is mounted in body 16. Plunger 66 has an elongate stem 68, which fits within bore 42, and a cap 70, which adjoins flange 18. Cap 70 is continuous with the forward end of stem 68. Cap 70 has a circumferential margin 72 and, to the rear, a clamp surface 74, that faces and overlaps or partially overlaps clamp surface 24 of flange 18 and a base surface 76 that is disposable against base surface 26 of flange 18. Clamp surfaces 74, 24, boss shoulder 28, and the outermost portion of base surfaces 76, 26 are complementary in shape so as to function as a clamp and seat for acetabular reamer cup base 12. In a particular embodiment of the invention suitable for use with curved bottom acetabular reamer cups 12, clamp surfaces 74, 24 are planar and radially of longitudinal axis 14 and are small. In that embodiment, base surfaces 76, 26 are complementary, concave and convex, respectively. Openings may extend through cap 70 for cleaning. In one particular embodiment, both cap 70 and flange 18 are both hexagonal and of the same size with cap 70 rotated about 30° from flange 18. In another particular embodiment, both cap 70 and flange 18 are octagonal and of the same size with cap 70 rotated about 45° from flange 18.

Stem 68 of plunger 66 has outer and middle portions 78, 80. Outer portions 78 are cylindrical in shape and fit closely in respective main bore sections 46. Middle portion 80 of stem 68 has the same diameter as outer portions 78. Extending through middle portion 80 perpendicular to longitudinal axis 14, is a stem slot 82. Stem slot 82 has a uniform, oval cross-section in directions parallel to longitudinal axis 14. The longest dimension of stem slot 82 is parallel to longitudinal axis 14 and is about two-thirds the length of the longest dimension of shaft slot 50. Stem slot 82 has forward and rear primary engagement edges 84, 86 at forward and rear ends of stem slot 82.

A pair of opposed, cylindrical ball ports 88 extend into middle portion 80 of stem 68, perpendicularly of longitudinal axis 14 and stem slot 82. Ball ports 88 communicate with stem slot 82 at approximately the axial midpoint of stem slot 82. Interposed in each ball port 88 is a detent ball or detent rotary element 90. The diameter of detent balls 90 is less than the diameter of ball ports 88, but greater than the width of stem slot 82. Detent balls 90 are thus sized so as to be able to rotate and move linearly within ball ports 88, but are too large to enter and move along stem slot 82. Ball ports 88 and detent balls 90 together act as a detent mechanism 92.

Below stem slot 82, middle portion 80 of stem 68 has a recess 94, which extends inwardly from the maximum diameter of stem 68. Below recess 94 is a stem wedge surface 96, which is angled outwardly and rearwardly from recess 94 to an outer portion 78. The axial length of recess 94 and stem wedge surface 96 together is greater than the diameter of lock balls 60. The radial separation of stem wedge surface 96 and the outside surface 98 of shaft wall 44 is everywhere less than the diameter of lock balls 60. In a particular embodiment of the invention, recess 94 and stem wedge surface 96 each encircle stem 68.

An actuator 100 encircles shaft 20 behind flange 18. On the inside, actuator 100 has front and rear inside contact surfaces 102, 104, a notch 106, a recess 108 and an actuator wedge surface 110. On the outside, actuator 100 has an outside contact surface 112 and a grip 114. Inside contact surfaces 102, 104 and outside contact surface 112 closely adjoin and are slideable along shaft 20 and collar 62, respectively, therebetween.

Outside contact surface 112 extends most of the length of actuator 100. Grip 114 is to the rear of outside contact surface 112 and is engaged by the user's thumb. In a particular embodiment of the invention, grip 114 is sloped rearwardly and inwardly.

Notch 106 is at the front of actuator 100, adjoining shaft 20, and engages spring 64. Spring 64 is loaded, that is, partially compressed between actuator 100 and boss 22, so that spring 64 biases actuator 100 toward the rear in all positions of actuator 100.

Front inside contact surface 102 adjoins notch 106 to the rear. Actuator 100 has an axial length to the rear of notch 106, greater than the axial length of shaft 20 from flange 18 to the rear surface or ball receivers 58, less the axial length of spring 64 when fully compressed. Behind front inside contact surface 102, actuator wedge surface 110 is slanted outwardly and rearwardly to recess 108. Actuator wedge surface 110 are both angled relative to and roughly parallel to stem wedge surface 96.

Rear inside contact surface 104 is to the rear of recess 108. The total axial length of recess 108 and actuator wedge surface 110 is about the same or longer than the axial length of shaft slot 50. The radial separation of recess 108 from bore 42 is slightly greater than the diameter of lock balls 60. The radial separation of wedge surface 110 from bore 42 is everywhere less than the diameter of lock balls 60. In a particular embodiment of the invention, recess 108 and wedge surface 110 are annular in shape and encircle actuator 100.

A pin or follower 116 extends through actuator 100 perpendicular to longitudinal axis 14. Pin 116 is an allen screw or similar fastener having threads at one end, a head with a recessed socket at the other end, and a cylindrical portion therebetween. Actuator 100 has a pair of complementary, opposed holes 118. Pin 116 extends through shaft slot 50 and stem slot 82 and retains plunger 66 in bore 42 of shaft 20.

The primary diameter of pin 116, the diameter behind the head, is slightly less than that of slots 50, 82 and pin 116 is freely slideable along slots 50, 82 in an axial direction. The primary diameter of pin 116 is also slightly less than the diameter of main portion 62 of enlarged bore section 48 less the sum of the diameters of both detent balls 90.

Figure 2:
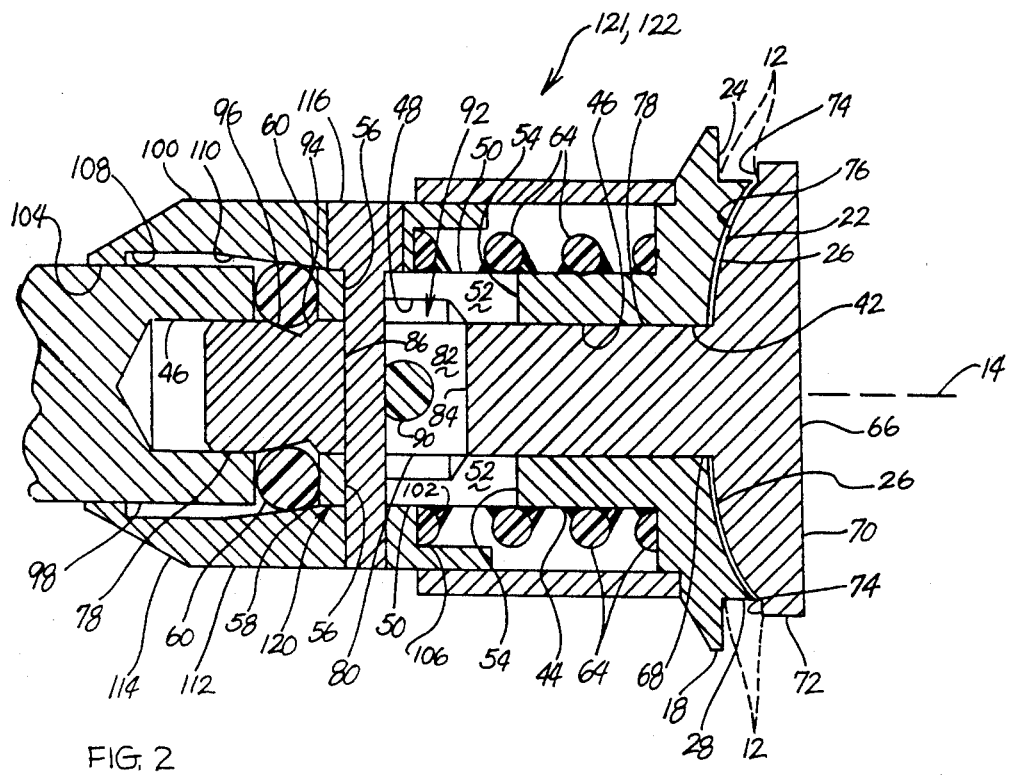
FIG. 2 is a cross-sectional view of the tool driver of FIG. 1 taken substantially along line 2—2 of FIG. 1. The plunger is in its retracted position and the actuator is in its retracted and locked position.
Figure 3:
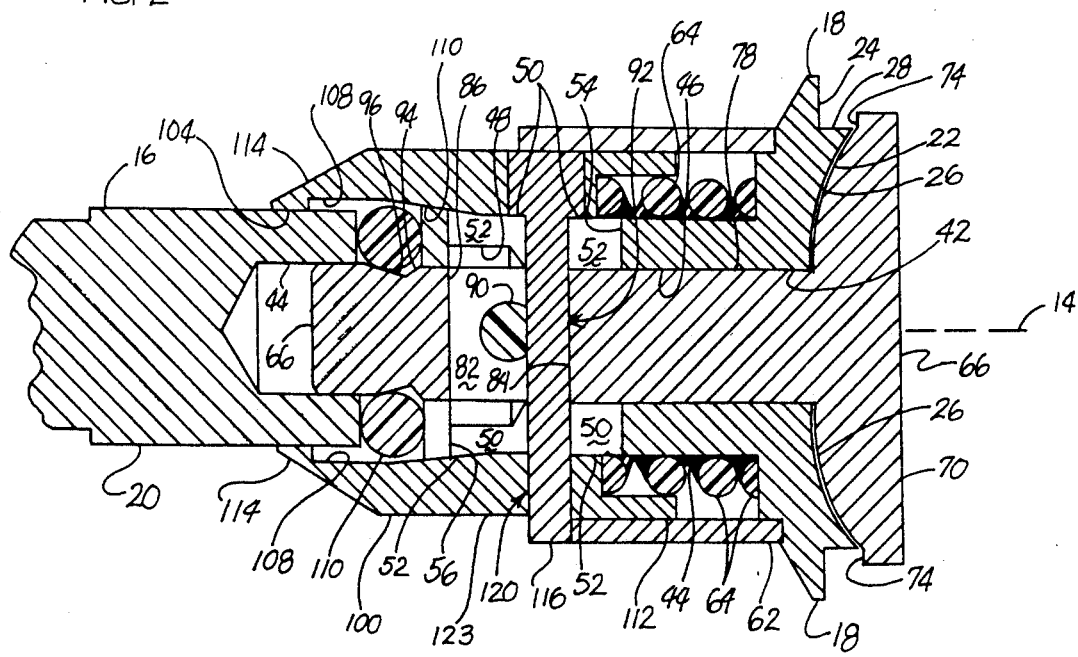
FIG. 3 is a partial view of the same cross-section as FIG. 2. The plunger is in its retracted position. The actuator is in its extended position.
Figure 4:
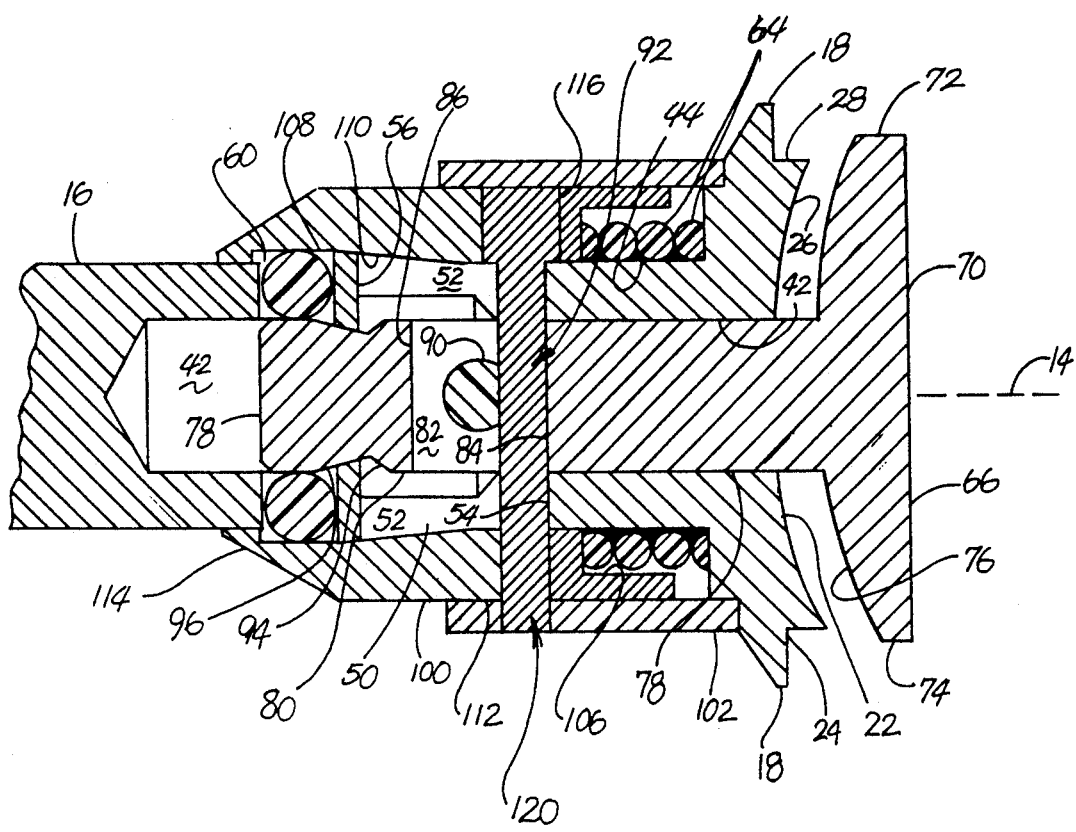
FIG. 4 is a partial view of the same cross-section as FIG. 2. The plunger and actuator are in extended position.
Figure 5:
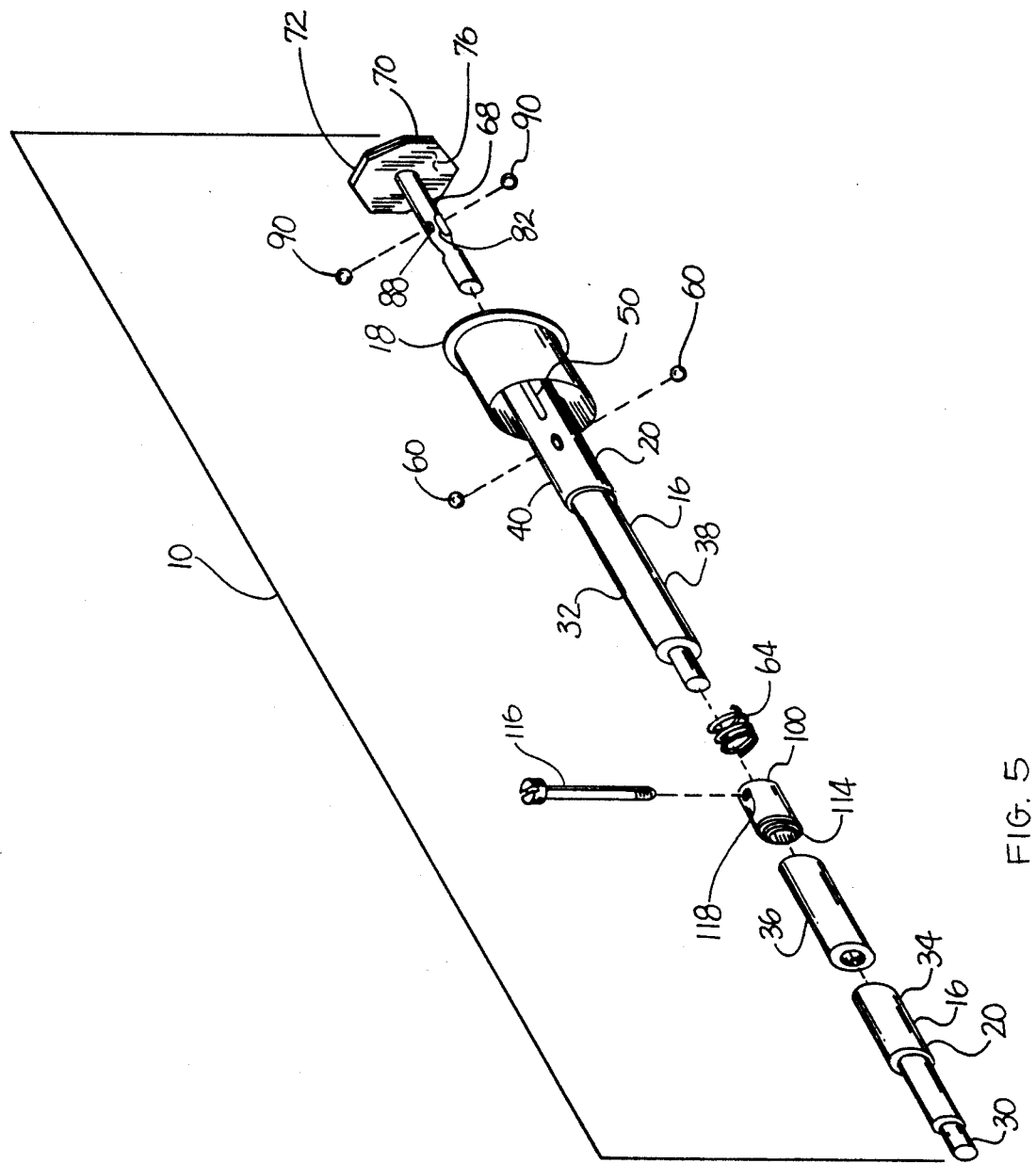
FIG. 5 is an exploded view of the tool driver of FIG. 1.

Referring now to FIGS. 2-4, pin or follower 116 and primary and secondary engagement edges 84, 86 and 54, 56, respectively, together define a coupling 120, which joins body 16, plunger 66 and actuator 100. Coupling 120 is loose, that is, allows relative movement, in an axial direction, since pin 116 is movable axially within slots 50, 82. Actuator 100 can move axially, independently of plunger 66 between a locked and retracted position 122, shown in FIG. 2, and a extended position 123, shown in FIG. 3. In locked position 122, actuator 100 substantially immobilizes plunger 66 relative to body 16. In extended position 123, plunger 66 is freely movable forward a distance equal to the axial length of stem slot 82, by the application of a slight force by the user or by the action of gravity on an appropriate positioned driver 10. Plunger 66 is movable, along longitudinal axis 14 and relative to body 16, from retracted position 124 to an extended position 126, shown in FIG. 4.

Maximum axial movement of actuator 100 by itself and of actuator 100 and plunger 66 together is determined by the axial movement of pin 116 in slots 50, 82. Pin or follower 116 engages both rear engagement edges 86, 56 in locked position 122. Pin 116 engages front primary engagement edge 84 and is disengaged from secondary engagement edges 54, 56 in extended position 123, as shown in FIG. 3, and may engage both front engagement edges 54, 84 when plunger is in its extended position 126. Body 16, plunger 66 and actuator 100 are substantially precluded by coupling 120 from relative rotation about longitudinal axis 14.

In locked position 122, actuator 100 is biased rearwardly by spring 64. Actuator 100 immobilizes plunger 66 by the engagement of wedge surfaces 96, 110 against opposite sides of each lock ball 60. Since wedge surfaces 96, 110 are angled relative to each other and yet roughly parallel, relative axial movement narrows or widens the separation between wedge surfaces 96, 110. In locked position 122, the separation of wedge surfaces 96, 110 is at a minimum and lock balls 60 are tightly clamped, which interlocks and jams wedge surfaces 96, 110 in juxtaposition. A force applied to plunger 66, in a forward direction relative to actuator 100, tends to rotate lock balls 60 in a forward and outward direction, which in turn tends to drive actuator 100 rearwards, further tightening the grip of wedge surfaces 96, 110 on lock balls 60.

When actuator 100 is moved into extended position 123, lock balls 60 are released by actuator wedge surface 110. If plunger 66 is then pulled outward, lock balls 60 rotate in an outward and forward direction and lock balls 60 move radially outward as stem wedge surface 96 is pulled past. Lock balls 60 move in the same manner when actuator 100 and plunger 66 are both moved from retracted position 121, 124 to extended position 123, 126. Movement of actuator 100 from locked position 122 to retracted position 121 moves pin 116 from a position to the rear and adjoining or contiguous detent balls 90 to a position to the front and adjoining or contiguous with detent balls 90. During this movement of pin 116, detent balls 90 rotate within ball ports 88 and move radially outwardly. Main portion 62 of enlarged bore section 48 is sized so as to accommodate this radial movement of detent balls 90. In a particular embodiment of the invention, middle portion 80 has a diameter equal to the sum of the diameters of the two detent balls 90 plus the primary diameter of pin 116. In that embodiment of the invention, detent balls 90 briefly engage inside wall surface 52 of shaft 20 as pin 116 moves past balls 90, and balls 90 close a portion of slot 50 when balls 90 are positioned in front of pin 116 thereby transforming slot 50 from a free passage slot to a hole. The transformation of slot 50 to a hole prevents plunger 66 from moving further outwardly. This transformation also secures plunger 66, actuator 100 and pin 116 together in the locked position 122 The, increased resistance which the user must overcome the resiliency of spring 64 in moving actuator 100 from locked position 122 to an extended position 123 as shown in FIG. 4 helps avert unintentional movement of plunger 66.

Rearward movement of plunger 66 from extended position 126 to retracted position 124 and of actuator 100 from to its locked position 122 is the reverse of the above-described forward movements. In a particular embodiment where flange 18 and cap 70 are similarly sloped and sized, cap 70 and flange 18 are aligned in extended position 126 and misaligned in retracted position 124 and locked position 122. In another particular embodiment, slot 50 is helical of shaft 20 and is used to accomplish rotation of multiples of about 30° where flange 18 and cap 70 are hexagonal and multiples of about 45° when flange 18 and cap 70 are octagonal, during the movement of plunger 66 and actuator 100 between locked position 122 to extended position 126.

In use, the actuator 100 is first pushed forward from locked position 122 by the user. This may easily be done by the user wrapping the fingers of one hand around sleeve 36 of actuator 100 and pushing against grip 114 with the thumb of the same hand. Actuator 100 and plunger 66 may then be pushed forward from locked position 122 by continuing forward movement of the user's thumb. Actuator 100 and plunger 66 may then be held against the action of spring 64 by the user's thumb, while the opening in acetabular reamer cup base 12 is placed against circumferential margin 72 of plunger cap 70. Acetabular reamer cup 12 is moved rearward and seated against clamp surface 24 and boss shoulder 28. If cap 70 does not rotate relative to flange 18 during movement between lock position 122 and extended position 120, then rotation of cup 12 will be necessary to seat cup 12 against clamp surface 24. The user may then reduce the force applied by thumb against grip 114 of actuator 100 and allow spring 64 to move actuator 100 and plunger 66 rearward until clamp surfaces 24, 74 grasp acetabular reamer cup 12 and actuator 100 is in its locked position 122. Acetabular reamer cup 12 and driver 10 may then be used. After use, a similar procedure is utilized to release acetabular reamer cup 12. Reamer cup 12 can then be disassembled from driver 10. Driver 10 can then be disassembled for cleaning, if desired, and reused.

In locked position 122, shown in FIG. 2, actuator 100 is at its maximum rearward travel and pin 116 engages rear engagement edges 86, 56. In retracted position 124, shown in FIG. 3, plunger 66 is at its maximum rearward travel, but pin 116 is in its most forward position and engages front primary engagement edge 84. If, however, acetabular reamer cup 12 has an axial dimension greater than that of boss shoulder 28, full rearward travel of plunger 66 is not possible and the location of plunger 66 is forward of that shown in FIGS. 2 and 3. This changes the point of contact between stem wedge surface 96 and each lock ball 60, which in turn moves lock balls 60 radially outward and changes the point of contact between actuator wedge surface 110 and each lock ball 60. This prevents full rearward travel of actuator 100. The net result is a locked position (not shown) forward of that shown in FIG. 2. This shifting forward of locked position 122, to accommodate the thickness of acetabular reamer cup 12, is subject to a limit determined by the axial length of plunger wedge surface 96.

In extended position 126, shown in FIG. 4, plunger 66 is 167 at their maximum forward travel. Actuator 100 is also in its most forward position with pin 116 is against forward engagement edges 84, 54. Extended positions (not shown) of actuator 100 and plunger 66 to the rear of those shown in FIG. 4, may be achieved by lesser forward movement of the user's thumb.

The improved tool driver of the invention both tightly grips and easily releases tools like an acetabular reamer cup, all with one hand, the tool driver tends not to collect bone debris, but can be completely disassembled for cleaning if necessary.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A tool driver comprising a body having a bore, said bore having a longitudinal axis, a plunger disposed in said bore, said body and said plunger having a lock, an actuator disposed on said body, said actuator and said plunger being loosely coupled thereby forming a loosely coupled mechanism, said loosely coupled mechanism being axially movable together relative to said body between an extended position and a retracted position, said actuator having a locked position, said plunger when said actuator is in said locked position being substantially immobilized relative to said body in directions moving said plunger away from said body, said locked position being anywhere between and including said retracted position and said extended position, and a spring resiliently urging said loosely coupled mechanism toward said retracted position, whereby tools of any thickness less than the distance between said extended position and said retracted position can be both clamped and locked between said plunger and said body.

2. The tool driver of claim 1 wherein said body and plunger have opposed clamp surfaces, said movement of said plunger between said extended position and said retracted position varying the separation of said clamp surfaces.

3. The tool driver of claim 2 wherein said actuator and said plunger have wedge surfaces, said wedge surfaces being jammed in juxtaposition in said locked position.

4. The tool driver of claim 2 wherein said actuator has an inwardly facing wedge surface and said plunger has an outwardly facing wedge surface.

5. The tool driver of claim 3 further comprising a rotary lock element disposed in fixed axial relation to said body, said rotary lock element being gripped between said wedge surfaces in said locked position.

6. The tool driver of claim 1 further comprising a detent mechanism disposed internal to said actuator, said detent mechanism resisting movement of said plunger relative to said body.

7. A tool driver comprising a body having a longitudinal axis and opposite ends, said body having a flange extending radially outwardly adjacent one of said ends and a shaft extending axially away from said flange toward said other end, said body having a bore extending toward said other end from said flange into said shaft, a plunger disposed in said bore, said flange and said plunger each having a clamp surface, said clamp surfaces being opposed, an actuator disposed on said body, a coupling loosely joining said actuator with both said plunger and said body, said coupling limiting relative movement of said body and said plunger and said actuator substantially to movement of said actuator and plunger relative to said body between an extended position and a retracted position, said actuator having a locked position, said actuator in said locked position substantially immobilizing said clamp surfaces from movement in directions away from each other, said movement of said plunger relative to said body between said extended position and said retracted position varying the separation of said clamp surfaces, said locked position being anywhere between and including said retracted position and said extended positions and a spring resiliently urging said actuator toward said retracted positions whereby tools of any thickness less than the distance between said extended position and said retracted position can be both clamped and locked between said clamp surfaces.

8. The tool driver of claim 7 wherein said coupling further comprises a follower, said body having axially spaced apart forward and rearward primary engagement edges, and said shaft having axially spaced apart forward and rearward secondary engagement edges, said follower engaging said forward primary engagement edges and being disengaged from said secondary engagement edges in said extended position, said follower engaging both said rearward engagement edges in said retracted position.

9. The tool driver of claim 8 wherein said follower is releasably joined in rigid relation to said actuator.

10. The tool driver of claim 8 further comprising a detent mechanism resisting movement of said follower between said engagement edges.

11. The tool driver of claim 8 wherein said follower engages both said rear engagement edges in said locked position.

12. The tool driver of claim 7 wherein said actuator and said plunger have oppositely oriented wedge surfaces, said wedge surfaces substantially precluding movement of said plunger relative to said actuator and said body in said locked position.

13. The tool driver of claim 7 wherein said actuator and said plunger have wedge surfaces, said wedge surfaces being jammed in juxtaposition in said locked position.

14. The tool driver of claim 13 further comprising a rotary lock element disposed in fixed axial relation to said body, said rotary lock element being gripped between said wedge surfaces in said locked position.

15. The tool driver of claim 14 wherein said rotary lock element is spaced apart from at least one of said wedge surfaces in said retracted position.

16. The tool driver of claim 7 further comprising a collar extending rearwardly from said flange in spaced relation to said shaft and a spring disposed within said collar, said spring encircling said shaft.

17. The tool driver of claim 16 wherein said collar encircles said actuator.

18. The tool driver of claim 2 wherein said actuator and said plunger have spaced apart wedge surfaces, said wedge surfaces being jammed in juxtaposition in said locked position, said wedge surfaces being jammed in juxtaposition in said extended position.

19. The tool driver of claim 2 wherein said plunger and said actuator have wedge surfaces, said wedge surfaces being jammed in juxtaposition in said extended position.

20. The tool driver of claim 8 wherein said follower is a pin extending through said actuator, said body, and said plunger.

* * * * *